(12) United States Patent  
Foulkes et al.

(10) Patent No.: US 12,290,316 B2  
(45) Date of Patent: May 6, 2025

(54) MEDICAL OPHTHALMIC DEVICE

(71) Applicant: SCOUTCAM LTD., Omer (IL)

(72) Inventors: Richard Foulkes, Lombard, IL (US); Amir Govrin, Ramat Gan (IL); Yekaterina Dlugach, Mabuim (IL)

(73) Assignee: SCOUTCAM LTD., Omer (IL)

( * ) Notice: Subject to any disclaimer, the term of this patent is extended or adjusted under 35 U.S.C. 154(b) by 551 days.

(21) Appl. No.: 17/606,236

(22) PCT Filed: Apr. 30, 2020

(86) PCT No.: PCT/IL2020/050483  
§ 371 (c)(1),  
(2) Date: Oct. 25, 2021

(87) PCT Pub. No.: WO2020/222238  
PCT Pub. Date: Nov. 5, 2020

(65) Prior Publication Data  
US 2022/0257416 A1 Aug. 18, 2022

Related U.S. Application Data

(60) Provisional application No. 63/001,583, filed on Mar. 30, 2020, provisional application No. 62/841,523, filed on May 1, 2019.

(51) Int. Cl.  
*A61F 9/007* (2006.01)  
*A61B 3/00* (2006.01)  
(Continued)

(52) U.S. Cl.  
CPC ............. *A61B 3/10* (2013.01); *A61B 3/0008* (2013.01); *A61B 3/145* (2013.01);  
(Continued)

(58) Field of Classification Search  
CPC ......... A61B 3/10; A61B 3/0008; A61B 3/145; A61B 1/06; A61B 2217/005;  
(Continued)

(56) References Cited

U.S. PATENT DOCUMENTS 4,340,037 A 7/1982 Lewicky  
4,607,622 A 8/1986 Fritch et al.  
(Continued)

FOREIGN PATENT DOCUMENTS

CN 2885155 Y 4/2007  
CN 103976763 8/2014  
(Continued)

OTHER PUBLICATIONS

Sugar, A. (2016) 2-6 Hydrodissection and Hydrodelineation, Syrian Board of Ophthalmology in YouTube web page, minutes: 0:43-1:46, https://www.youtube.com/watch?v=YpiCkOAq9dQ.  
(Continued)

*Primary Examiner* — Scott M. Getzow  
(74) *Attorney, Agent, or Firm* — The Roy Gross Law Firm, LLC; Roy D. Gross

(57) ABSTRACT

A tool comprising a handpiece having a flattened cannulated tip that is adapted to receive flow from a pumping unit, in order to generate a jet of fluid suitable for procedures such "hydro-dissecting" cells in the eye. According to an embodiment of the invention, the tool comprises a visualization probe with at least one camera, wherein the sensor of the at least one camera is distally located at the tip of the tool to be inserted in to the eye for imaging from within the eye.

21 Claims, 11 Drawing Sheets

(51) Int. Cl.
  *A61B 3/10* (2006.01)
  *A61B 3/14* (2006.01)
  *A61B 1/06* (2006.01)
(52) U.S. Cl.
  CPC ...... *A61F 9/00736* (2013.01); *A61F 9/00745* (2013.01); *A61F 9/00781* (2013.01); *A61B 1/06* (2013.01); *A61B 2217/005* (2013.01); *A61B 2217/007* (2013.01)
(58) Field of Classification Search
  CPC ... A61B 2217/007; A61B 1/05; A61B 1/0684; A61B 1/07; A61B 3/1176; A61F 9/00736; A61F 9/00745; A61F 9/00781; A61F 9/008; A61M 1/774; A61M 2210/0612
  See application file for complete search history.

(56) References Cited

U.S. PATENT DOCUMENTS

| | | | |
|---|---|---|---|
| 4,779,612 A | 10/1988 | Kishi | |
| 4,867,138 A | 9/1989 | Kubota et al. | |
| 4,884,133 A | 11/1989 | Kanno et al. | |
| 4,950,278 A | 8/1990 | Sachse et al. | |
| 5,143,054 A | 9/1992 | Adair | |
| 5,217,465 A | 6/1993 | Steppe | |
| 5,254,106 A * | 10/1993 | Feaster | A61F 9/00736 604/272 |
| 5,284,476 A * | 2/1994 | Koch | A61F 9/00736 606/166 |
| 5,323,766 A | 6/1994 | Uram | |
| 5,331,950 A | 7/1994 | Wood, Sr. | |
| 5,575,756 A | 11/1996 | Karasawa et al. | |
| 5,593,402 A | 1/1997 | Patrick | |
| 5,685,823 A | 11/1997 | Ito et al. | |
| 5,716,320 A | 2/1998 | Buttermore | |
| 5,797,849 A | 8/1998 | Vesely et al. | |
| 6,217,584 B1 | 4/2001 | Nun | |
| 6,398,721 B1 | 6/2002 | Nakamura et al. | |
| 6,447,445 B1 | 9/2002 | Hirano | |
| 7,954,607 B2 | 11/2011 | Kallioniemi et al. | |
| 8,226,548 B2 | 7/2012 | Kuckliek | |
| 8,622,896 B1 | 1/2014 | Termanini | |
| 9,750,638 B2 | 9/2017 | Bourne et al. | |
| 10,492,662 B2 | 12/2019 | Govrin et al. | |
| 11,129,519 B2 | 9/2021 | Wei et al. | |
| 11,771,303 B2 | 10/2023 | Williams | |
| 2002/0094119 A1 | 7/2002 | Sahadevan | |
| 2003/0088260 A1 | 5/2003 | Smedley et al. | |
| 2006/0020165 A1 | 1/2006 | Adams | |
| 2007/0015961 A1 | 1/2007 | Yamamoto et al. | |
| 2007/0129605 A1 | 6/2007 | Schaaf | |
| 2007/0167681 A1 | 7/2007 | Gill et al. | |
| 2008/0091074 A1 | 4/2008 | Kumar et al. | |
| 2008/0167527 A1 | 7/2008 | Slenker et al. | |
| 2008/0214891 A1 | 9/2008 | Slenker et al. | |
| 2009/0097806 A1 | 4/2009 | Mellerobe et al. | |
| 2009/0253964 A1 | 10/2009 | Miyamoto | |
| 2009/0259097 A1 | 10/2009 | Thompson | |
| 2010/0305503 A1 | 12/2010 | Fang et al. | |
| 2010/0331658 A1 | 12/2010 | Kim et al. | |
| 2011/0063428 A1 | 3/2011 | Sonnenschein et al. | |
| 2011/0112405 A1 | 5/2011 | Barthe et al. | |
| 2011/0152618 A1 | 6/2011 | Surti | |
| 2012/0265010 A1 | 10/2012 | Uram | |
| 2012/0289858 A1 | 11/2012 | Ouyang et al. | |
| 2013/0205936 A1 | 8/2013 | Schmieding et al. | |
| 2014/0236163 A1 * | 8/2014 | Olson | A61F 2/1662 606/107 |
| 2014/0296866 A1 | 10/2014 | Salman et al. | |
| 2014/0309649 A1 * | 10/2014 | Alvarez | A61B 34/30 606/107 |
| 2015/0025539 A1 | 1/2015 | Alvarez et al. | |
| 2015/0045820 A1 | 2/2015 | Kahook | |
| 2015/0141755 A1 | 5/2015 | Tesar | |
| 2015/0297407 A1 | 10/2015 | Saimovici | |
| 2016/0143778 A1 | 5/2016 | Aljuri et al. | |
| 2016/0166134 A1 | 6/2016 | Sonnenschein et al. | |
| 2016/0287332 A1 | 10/2016 | Griffits | |
| 2017/0231477 A1 | 8/2017 | del Nido et al. | |
| 2018/0055596 A1 | 3/2018 | Johnson | |
| 2018/0078410 A1 | 3/2018 | Gavanescu | |
| 2018/0110404 A1 | 4/2018 | Devaiah et al. | |
| 2018/0125707 A1 | 5/2018 | Khaderi et al. | |
| 2019/0136070 A1 | 5/2019 | Aizenberg et al. | |
| 2019/0247229 A1 * | 8/2019 | Abt | A61F 9/00727 |
| 2019/0298321 A1 | 10/2019 | Intintoli et al. | |

FOREIGN PATENT DOCUMENTS

| | | |
|---|---|---|
| CN | 104224441 | 12/2014 |
| CN | 204207828 U | 3/2015 |
| EP | 1794486 B1 | 4/2011 |
| GB | 2268883 | 1/1994 |
| JP | H07-100096 | 4/1995 |
| JP | H09-238896 | 9/1997 |
| JP | 2009-056255 | 3/2009 |
| JP | 200956121 A | 11/2009 |
| JP | 2017-185024 A | 10/2017 |
| RU | 2177286 C2 | 2/2001 |
| WO | 200271991 | 9/2002 |
| WO | 2004026125 | 4/2004 |
| WO | 2011/033513 A1 | 2/2013 |
| WO | 2017100651 | 6/2017 |

OTHER PUBLICATIONS

Aisco opthalmic surgical Instruments catalog 2013, pp. 152-154. Retrieved Nov. 22, 2021 from: http://eyeco.com.mx/pdf/ASICO-Ophthalmic-Surgical-Instruments-Catalog-20131.pdf.
Geuder Ophthalmic Surgical Products-Instruments Main Catalog 2018, pp. 192-194. Retrieved Nov. 22, 2021 from: https://simovision.com/assets/Uploads/ Brochure-Geuder-Ophthalmic-Surgical-Instruments-EN2.pdf>.
Hydrodissection, Boston University School of Medicine, Department of Ophthalmology, webpage, Mar. 8, 2019; Retrieved Nov. 22, 2021 from: https://web.archive.org/web/20190308120225/http://www.bu.edu/eye/phacoprimer/hydrodissection/.
PCT International Search Report for International Application No. PCT/IL2020/050483, mailed Sep. 6, 2020, 12 pp.
PCT Written Opinion for International Application No. PCT/IL2020/050483, mailed Sep. 6, 2020, 9pp.
PCT International Preliminary Report on Patentability for International Application No. PCT/IL2020/050483, issued Sep. 9, 2021, 24pp.

* cited by examiner

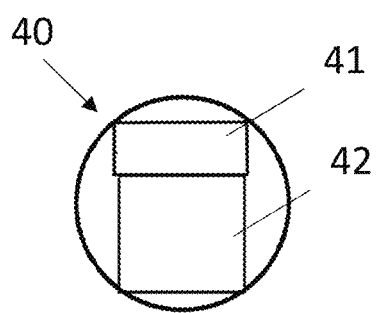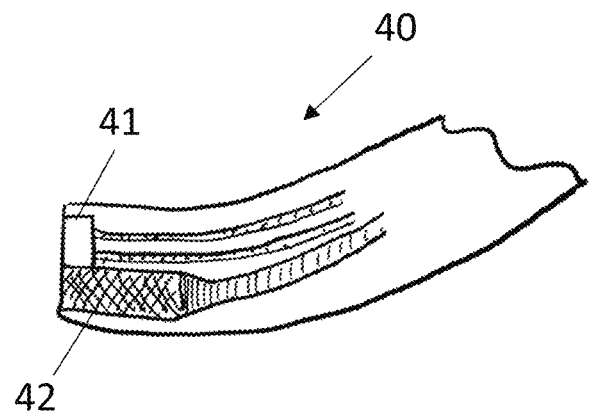
Fig. 4B  Fig. 4A
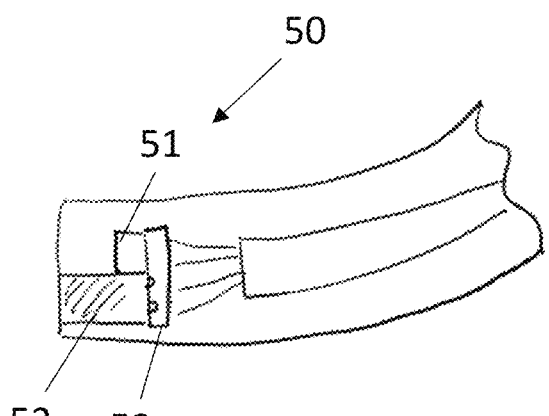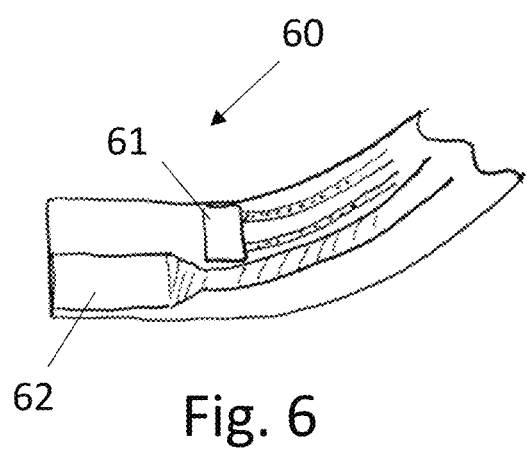
Fig. 5  Fig. 6

MEDICAL OPHTHALMIC DEVICE

CROSS REFERENCE TO RELATED APPLICATIONS

This application is a National Phase of PCT Patent Application No. PCT/IL2020/050483 having International filing date of Apr. 30, 2020, which claims the benefit of priority of U.S. Provisional Application Nos. 63/001,583 filed on Mar. 30, 2020 and 62/841,523 filed on May 1, 2019. The contents of the above applications are all incorporated by reference as if fully set forth herein in their entirety.

FIELD OF THE INVENTION

The invention relates to the field of medical tools. More particularly, the invention relates to a medical ophthalmic device useful in diagnostic, therapeutic and in surgical apparatus suitable for different human and/or animal medical/surgical procedures.

BACKGROUND OF THE INVENTION

Miniaturization can be a key to successfully performing precision medical procedure such as surgery (i.e., to a high resolution), especially in an intricate organ such as the eye. Moreover, it is well known that visualization inside the human body is an indispensable tool to enable the physician to perform an accurate diagnosis of a variety of illnesses, to deliver therapeutic agents and/or to perform minimal invasive surgical operations inside the body, as well as enabling surgical techniques that limit the size of incisions needed and so lessen wound healing time, associated pain and risk of infection, and even reducing or obviating the need for suture.

Cataract surgery is one of the most commonly performed procedures around the world. Over 4 million procedures are performed in the United States alone and it remains one of the leading causes of sight loss around the world. To remove a cataract by modern techniques a tool was developed in the 1970's and advanced over the past 40 years called a phacoemulsifier. This tool can enter the eye through a 2.5 mm pocket incision in the cornea and uses ultrasound to break up the cataract material and then vacuums these out of the eye. The cataract is supported in the eye inside of a very thin membrane called the lens capsule. It is opened with a circular tear of at least 5.5 mm. The lens is separated somewhat by injecting water under the capsular rim to flow around the cataract. The lens is typically removed by making grooves through the middle then splitting the lens into halves or quarters. These are then separated using a second instrument though a smaller side incision of 1.0 to 1.5 mm. Once the lens nuclear or dense part of the lens is removed a smaller nozzled instrument is used that uses suction to strip the softer portion of the cataract off the delicate lens capsule. These cells that reside on the surface of the capsule are adherent and difficult to fully remove without violating the capsule. For this reason, they are normally reduced but not fully removed. The pupil of the eye under the influence of drops will dilate 6-10 mm and the lens is typically 12-13 mm in size. Therefor the lens material that resides under the iris is not easy to visualize. The surgeon may reach under the iris with the suctioning tool, but this maneuverer is risky as the capsule will become captured in the vacuum tip and may be damaged or torn. Once the capsule appears clear the "bag" is filled with a gel call viscoelastic and a 6 mm implant is extruded into the eye through the 2.5 mm incision. At this point the I/A tool is used again to remove the gel as it will cause elevated eye pressure as it dissolves in the first 24 hours after surgery. The gel is clear and it is very hard to visualize. It will adhere to the back of the lens and will be retained in the peripheral parts of the capsule and against the inner aspect of the cornea. The retained lens cells that are referred to as lens epithelial complex cells or LEC can be addressed with some effort using scraping tools or a round roughened ball call an Olive tip. Despite these efforts a secondary cataract will form in over half the eyes over the first few months to years of surgery.

To address this issue which causes glare and loss of best vision a laser was developed in Israel called the YAG laser. It is a disruptive laser that will open the capsule behind the implant and the capsule, and the cells will float into the back of the eye. The IOL will normally remain in place as it is secured by its 11 mm "arms" which reach out into the capsule. Once this procedure has been performed the vision normally improves but the patient will have "floaters" or debris floating in the vitreous. There is a low rate of retinal detachment and swelling of the center of vision called the macula. The IOL cannot now be easily exchanged because the vitreous will now be able to come into the front of the eye. In modern times we have developed IOL that can give a patient bifocal vision. These IOL's are not tolerated by all patients because they can cause halo's and glare. It is a leading cause of lens exchange in what is known as dyphotopsia. The clinical quandary is that when a patient has retained lens cells and this type of IOL it hard to know whether treating the capsule or exchange will improve their vision. If the capsule is treated, then the exchange of the IOL is made very difficult requiring a vitreous removal called vitrectomy. This further increase the risk of a decentered IOL or swelling in the retina.

It has been noted that using a flattened cannula and vigorously rinsing the capsule with water that the rate of retained cells can be reduced. The cells that are out of sight under the iris cannot be addressed as well. It is the object of the present invention to address this with a device specifically designed to improve intraocular visibility using a micro video camera to allow for visualizing and then power-washing of these cells and viscoelastic.

Glaucoma is a neurodegenerative loss of nerve fibers that are damaged when elevated eye pressure pushes on the optic nerve in the back of the eye. The fibers are thought to be "squeezed" and they enter a phase known as apoptosis or programmed cell death. It is a leading cause of sight loss around the world and the predilection increases with age parallel to the development of cataracts. The cause of the elevated pressure is reduction in the outflow system of the eye and a backup of aqueous fluid which elevates the pressure. Drops and laser can be used and in severe cases an opening can be made to allow the fluid to pass out of the eye under the conjunctiva. In the past 15 years devices have been developed to bypass the outflow tissue called the trabecular meshwork. This is called Minimally invasive glaucoma surgery or MIGS. There are variations but in general at the time of cataract surgery a device is placed through this meshwork or the meshwork is stripped away to give free passage of aqueous into venous collectors. To perform this maneuver is challenging as the angle of the eye cannot be seen while looking directly down from the microscope. Therefor a prism must be used as well as turning the patients head away from the scope 45 degrees and then tilting the microscope 45 degrees. Gel is placed on the cornea and the view of the angle will be captured. The inserting instrument is place under the prism, through the incision advanced across the eye and the device or the stripping is attempted. As this tissue is connected to veins with pressure on the surface often blood will flow back into the eye occluding the view of the angle. This must be cleared with viscoelastic and another attempt is made. It is the intent of this tool to provide a direct view of the angle without the need of tilting the head or microscope and as it can eject water and light the view of the intended target which will remain clear as the spraying system can clear any blood should it occur.

It is an object of the present invention to advance surgical techniques with one tool for performing efficient medical procedures, such as those described above as well as a myriad of other procedures where visibility through the microscope is limited by opacity, iris, blood and to reduce complications that may occur. One or more of the following features can be incorporated into this tool: a camera, light source, including color, laser source, scraping tool, irrigation (inflow and outflow) including pulsation, aspiration, ultrasound as well as injection of gas and/or drugs.

It is yet an object of the present invention to combine "power washing" of cells and viscoelastic from the lens capsule after cataract removal with the ability to distend the capsule to improve the efficacy and safety of removal of further dislodged cells that are hidden behind the iris or simply not visible from the microscope angle but easily seen from the angle of the camera enhanced at times by color to fluoresce the cells which are lipid covered from the capsule which is collagen.

It is still another object of the present invention to use controlled and targeted jetting of saline in eye surgery which can be used to open tissue planes and to clear blood and debris and remove residual viscoelastic trapped in the crevices normally missed by a suctioning tool.

It is still another object of the present invention to provide visualization of trabecular meshwork, the ciliary sulcus, Schlemm's canal, ciliary body and sub iris area to assist micro invasive glaucoma surgery. Camera device potentially can decrease for cumbersome tools like prisms to visualize the tissues not seen from a microscope. Combined optic vision to allow implants (stent), shunt or any other device reduces the eye pressure to be delivered and placed or to allow delivering the shunt.

It is still another object of the present invention to provide a medical ophthalmic device that is capable of accurately deliver drug under direct vision. This can be accomplished safely under direct observation internally. The needle insertion may come from a second hand using the needle. Clipping or otherwise securing a pump or medical device that dissolves medicine over lengthy periods of time could be accomplished easily with this video device.

It is still another object of the present invention to provide medical ophthalmic device that is capable of delivering laser power under direct vision to use in glaucoma, to repair tear in retina, to cauterize blood vessels.

It is a further object of the present invention to enable procedures to be standardized by being able to open and stabilize the anterior and posterior chamber with internal flow which will improve the opportunities for successful implementation of procedures in eye surgery.

It is a further object of the present invention to enable cataract surgery, glaucoma surgery and vitrectomy, tear duct opening, eye trauma and tumour surgery.

Other objects and advantages of the invention will become apparent as the description proceeds.

SUMMARY OF THE INVENTION

In a first aspect, the invention is a tool comprising a handpiece having a flattened cannulated tip that is adapted to receive flow from a pumping unit, in order to generate a jet of fluid suitable for "hydro-dissecting" cells in the eye.

According to an embodiment of the invention, the tool is adapted to aspirate cortical or cells from the capsule under an incision or to remove other debris/residual, such as residual viscoelastic trapped in the crevices.

According to an embodiment of the invention, the tool is a hydro-dissection micro camera tool.

According to an embodiment of the invention, the tool further comprises a channel configured to be connected to an external suction unit to suction fluid at a rate suitable to the ejectant.

In embodiments of the tool, the received flow is controlled before reaching the flattened cannulated tip of the handpiece.

In embodiments of the tool, the flow is controlled by a processing unit in accordance with inputs received from a controlling unit for allowing variation in flow to the flattened cannulated tip, wherein the volume of flow can vary depending on aperture of said flattened cannulated tip which affects velocity. The controlling unit can be a manual operated unit (e.g., a foot pedal), an automated/autonomous controlled unit (e.g., that may involve Artificial Intelligent), or any combination thereof.

In embodiments of the tool, the flow can pulse at variable rates adjustable by the controlling unit (e.g., by pressure applied to the foot pedal). As another example of this embodiment, a variety of sensors, in combination with machine learning, artificial intelligence (A.I.) and programmable software, can autonomously control and change the flow of said hydro-dissection endoscope tool. A database of program settings can be stored in a software package that allows the user to personalize their user preferences, that are each suitable for various stages of a particular surgical procedures In embodiments of the tool, the handpiece is designed to control the flow upon depression and release of a suitable element (e.g., a valve or an activating button), thereby leading to continuous flow at lower flow rates or faster flow as the pressure builds behind occlusion.

In embodiments of the tool, the flattened cannulated tip is replaceable, thus enabling for various tips to accomplish by narrowing of the flattened tip higher rates of thin dissecting flow, thereby enabling a surgeon to use the slit width and breadth that works best for their technique or procedure.

In embodiments of the tool, the opening of the slit may be straight or curved, elongated or narrow.

In embodiments of the tool, a redesigned phaco tip might allow for low level ultrasound with an ejection mode rather than suction or both.

According to an embodiment of the invention, the tool further comprises means for generating high frequency pulsation for removal of material that is adherent to surfaces, in particular lens cells.

In embodiments of the tool, the high frequency pulsation is generated by the pumping unit or by a rapid ball valve within the hand piece.

In embodiments of the tool, the rapid ball valve is tension loaded to allow for faster and slower pulsation.

In embodiments of the tool, the cannulated tip of the handpiece comprises a curved surface soft strip behind the tip for pushing cells loose after they have been loosened by the hydro-dissection on a distended capsule.

In embodiments of the tool, a ball valve system which opened with pressure within the handpiece could be controlled with a simple flow direction switch to choose continuous flow or pulsed flow through the same handpiece or could be a separate handpiece with this continuous capability.

In embodiments of the tool, the flattened cannulated tip is a bimanual tip with separation of the flow and suction.

In embodiments of the tool, the flattened cannulated tip is made of silicone or other soft synthetic material to allow for scraping as well as hydro-dissection from a softer tip.

According to an embodiment of the present invention, the tool further comprises a curved or straight band behind the tip to manually dislodge cells from the distended capsule.

In embodiments of the tool, the tip may be rotated to allow for expression under the incision.

In embodiments of the tool, a configuration of a bi-manual mode may be used with the irrigation and aspiration mode to allow for variable flow, wherein the bi-manual mode is controlled from a redesigned phaco machine for enhancing the effect of said bi-manual mode, by using positive pressure pumps for powering the flow into the tip with matching outflow.

In embodiments of the tool, the handpiece comprises a roughened area behind the tip that may be flattened to increase the surface area.

In embodiments of the tool, the tip may be made of soft flexible material or be made of hard plastic or metal material.

In embodiments of the tool, the tip may vary in width from about 0.5 mm to 1.8 mm, and wherein the tip's opening from about 0.05 mm to 1 mm.

In embodiments of the tool, the tip comprises a sleeve for removing fluid from the eye at the rate it is infused. This is the opposite of the current I/A tool.

According to an embodiment of the present invention, the tool further comprises a separate suction tip that may be used to remove debris and to enhance the ability to aspirate cortical or cells from the capsule under the incision.

In embodiments of the tool, the handpiece comprises a visualization probe to provide better visibility of the layer of cells that adhere.

In embodiments of the tool, the visualization probe comprises a video camera to visualize the capsule from the angle of ejection.

In embodiments of the tool, a light source may be white or chromatic to cause reflection/absorption of stained and unstained cells, wherein the light source can be integrated within the handpiece and/or the illumination can be provided from an external source.

In embodiments of the tool, the hydro-dissection tool is configured to enable bi-model arrangement to allow for suction and propulsion to work together, wherein the tip may be placed on an irrigation aspiration device to allow for this bi-model arrangement. In this mode the camera and ejection nozzle could be on one handpiece and the illumination and vacuum could be on the other handpiece. As will be appreciated by a person skilled in the art, any combination of these functions can be embodied, for example, the camera and the illumination can be located on one handpiece and the ejection nozzle and vacuum can be located on the other handpiece.

In embodiments of the tool the camera may incorporated on the tip of the I/A device designed to be bi modal allowing it perform irrigation and aspiration and then switch to hydro-dissection aspiration. In this form the same instrument may be used to perform when they are best utilized based on the surgeon's experience and need.

In embodiments of the tool, the tip may be placed on any ejection tool including I/A tool, a phaco tip, a syringe or an IV flow device elevated to provide pressure.

According to an embodiment of the present invention, the tool further comprises staining means for cells identification purposes, wherein staining means selected from the group consisting of illumination, staining material or combination thereof. Florescence can be enhanced by many stains and auto florescence can be noted to demarcate lipid cell walled lens cells from capsular collagen.

According to an embodiment of the present invention, the tool further comprises a semi flat surface with small holes to balance fluid outflow to inflow, remove lens cell material, fixate and scrape the capsule and scrape the capsule behind the soft scraping ridge.

According to an embodiment of the present invention, a shaft of a camera may be constructed of deformable plastic, metal, polyamides or articulating pieces that may be bent or rotated, e.g., to allow for 45 to 180 degree redirection, to allow the probe to visualize and treat area's underneath the incision without reentering the eye from the opposite side of the eye.

According to an embodiment of the present invention, the camera tip may be constructed of flexible material like rubber, silicone, hydrogels that will have lateral chords or wires that may be foreshortened to achieve any angle of view with rotation without withdrawing it from eye. The tube may have one or more articulating "elbows" that it may turn 90 to 180 degrees.

According to an embodiment of the present invention, the tool further comprises a dual sided scraping tool (e.g., which is about 0.1 to 0.3 mm) with suction behind one side of a vacuum port(s) (e.g., the vacuum port can be in form of a slit shape, holes or a larger opening) on the top side away from a scraping element to avoid capsular capture.

According to an embodiment of the present invention, the tool further comprises an attachment on which grasping or cutting tools may be attached to allow a view of the tips from the visualization probe, thereby enabling to perform tasks outside of view due to the iris. These may be bimanual.

In a second aspect the invention is a medical ophthalmic device, comprising at least one camera, wherein the sensor of the at least one camera is distally located at the tip of said camera, to be inserted in to the eye for imaging from within the eye.

In embodiments of the medical ophthalmic device the size of the device will be adjusted for the intent of its use. A larger device may be used for certain techniques though the primary incision. The device size will be guided by the utility required. Larger chips may provide higher resolution needed for certain procedures and normal resolution will be able to advance the multiple advantages through smaller incisions.

In embodiments of the medical ophthalmic device the body of the device is small enough to be inserted through the trocars used in vitrectomy surgery.

In embodiments of the medical ophthalmic device the diameter of said device is adapted to enable minimally invasive surgeries that employ surgical techniques that limit the size of incisions needed and so lessen wound healing time, associated pain and risk of infection. The incision size under 3 mm has been shown when properly constructed to give a watertight seal at the end of the surgery reducing or obviating the need for suture. Therefore, a medical device that can be applied through an incision of 3 mm or less provide for safety and minimal refractive change. All these embodiments will be able to be designed to provide full functionality based on the surgical goal and need.

In embodiments of the medical ophthalmic device the diameter of said device is less than about 1.8 mm. However, a larger version of the camera with a larger chip would be well under 3.0 mm.

In embodiments of the medical ophthalmic device an illumination source is incorporated in to said device.

In embodiments of the medical ophthalmic device the illumination source can be located distally (i.e., at the tip) or proximally (i.e., in the handpiece) of the device.

In embodiments of the medical ophthalmic device the distal illumination source is at least one Light-Emitting Diode (LED).

In embodiments of the medical ophthalmic device light reaches the distal end of the endoscope via optic fibres and/or light guides.

In embodiments of the medical ophthalmic device a phaco-emulsifier tool is integrated in to said device. The camera could be attached to the phaco tip to allow an internal view from that tip as determined to be effective.

According to embodiments of the invention, the medical ophthalmic device further comprises a tool for removing lens cells under direct vision. For example, this may be used in cases where corneal view is compromised from corneal swelling or staining in cases of blood.

In embodiments of the medical ophthalmic device the tool for removing lens cells under direct vision is an irrigation tool, an aspiration tool, or combination thereof.

In embodiments of the medical ophthalmic device the irrigation and aspiration are integrated together in concentric circles, i.e., one in the inner circle and one in the outer circle, or they are located adjacently but on the same tip. For example, these may be switchable to allow for ejection or vacuum to be switched as determined by the goal and experience of the surgeon.

In embodiments of the medical ophthalmic device the shape of an irrigation port is shaped to control the pressure.

In embodiments of the medical ophthalmic device the camera is attached to forceps and scissor tools.

In embodiments of the medical ophthalmic device the camera is attached to a cannula that is manually operated to provide ejection of water.

In embodiments of the medical ophthalmic device a laser device is incorporated in to said multi-purpose eye surgery device.

In embodiments of the medical ophthalmic device an external illumination source is adapted to provide illumination in accordance with the orientation of the device/camera.

In embodiments of the medical ophthalmic device a tube or the tip of the endoscope is made of a transparent polymer material, thus it can be used as light guiding generated by an illumination source.

In embodiments of the medical ophthalmic device the wavelength of the light can be varied.

BRIEF DESCRIPTION OF THE DRAWINGS

In the drawings:

FIG. 4A schematically illustrates a side of view of the tip of a medical ophthalmic device with camera and LEDs, according to an embodiment of the invention;

FIG. 4B schematically illustrates a cross section view of the tip of the medical ophthalmic device of FIG. 4A, according to an embodiment of the invention;

FIG. 5 schematically illustrates a side view of the tip of a medical ophthalmic device with camera and LED on the same PCB in one embodiment, according to an embodiment of the invention;

FIG. 6 schematically illustrates a side view of the tip of a medical ophthalmic device with camera and LED behind it, according to an embodiment of the invention;

DETAILED DESCRIPTION OF THE INVENTION

In one aspect, the invention described herein expands the functionality of the cannula approach by giving the surgeon continuous/pulsation flow from a pumping unit and control over force from the flow of fluid. The hydro-dissection tool (in any one of its embodiments) will be herein referred to as simply 'the tool'.

Figure 1A:
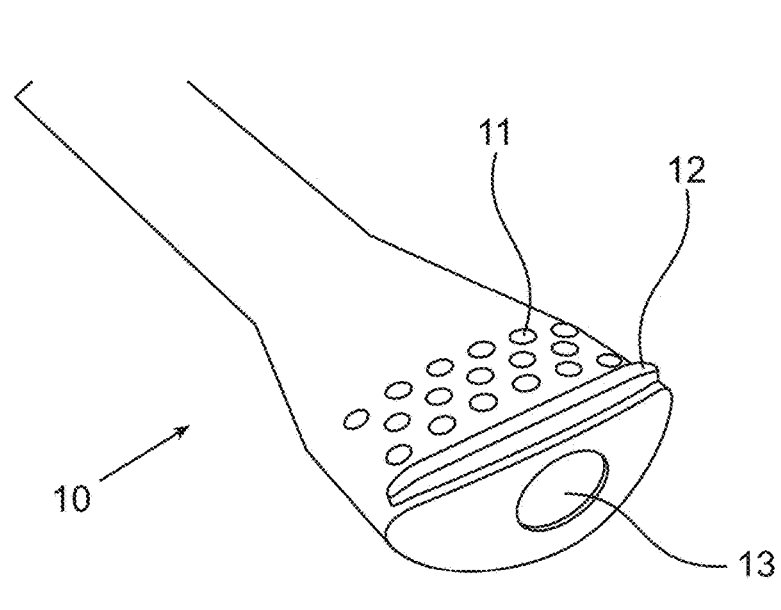
FIG. 1A schematically illustrates a perspective view of a head section of a hydro-dissection camera tool, according to an embodiment of the invention.
Figure 1B:
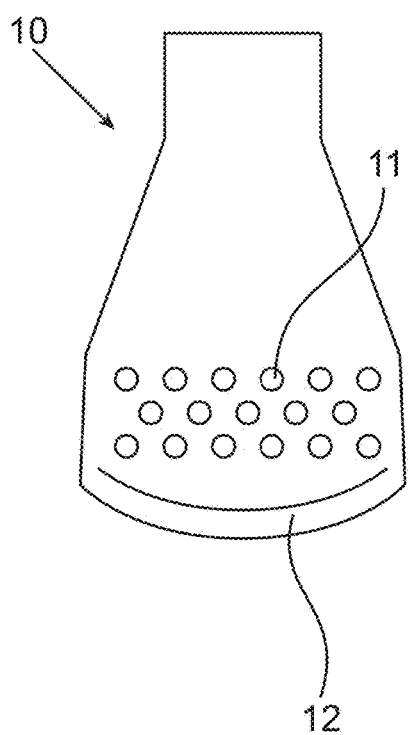
FIG. 1B schematically illustrates a top view of the head section of the hydro-dissection camera tool of FIG. 1A, according to an embodiment of the invention.
Figure 1C:
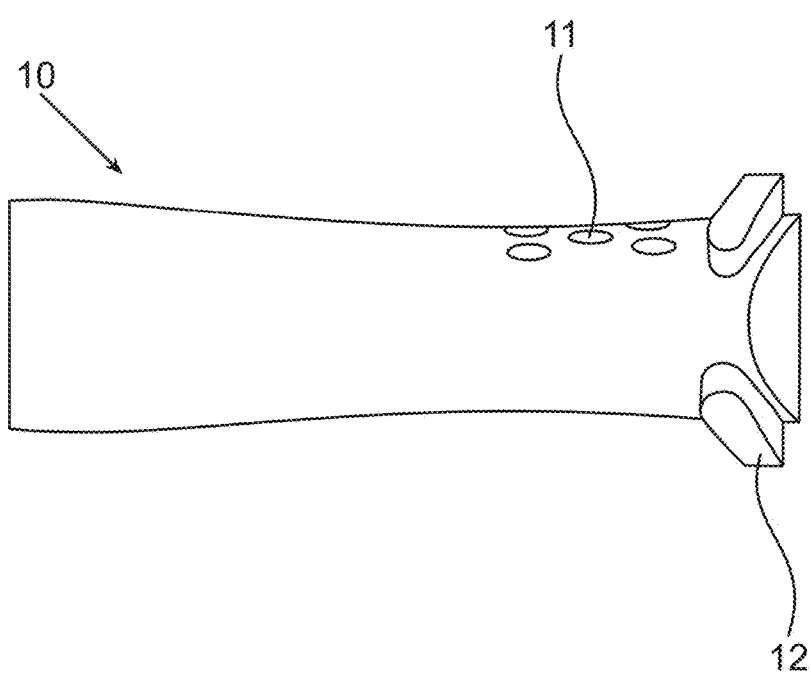
FIG. 1C schematically illustrates a side view of the head section of the hydro-dissection camera tool of FIG. 1A, according to an embodiment of the invention.

FIGS. 1A-1C schematically illustrate a head section of a hydro-dissection tool 10, according to an embodiment of the invention. The head section of hydro-dissection tool 10 comprises one or more vacuum ports 11, a soft and flexible scrubbing element 12 and a camera 13 located at the distal end of tool 10. In this embodiment, tool 10 has an elongated body suitable to be used as a handpiece. In this embodiment, the vacuum ports 11 are located on a top side away from element 12 to avoid capsular capture. In these figures, vacuum ports 11 are provided in form of holes, however, other form of vacuum ports or port can be employed, such as a slit shape or other form of openings suitable for suctioning.

Figure 2:
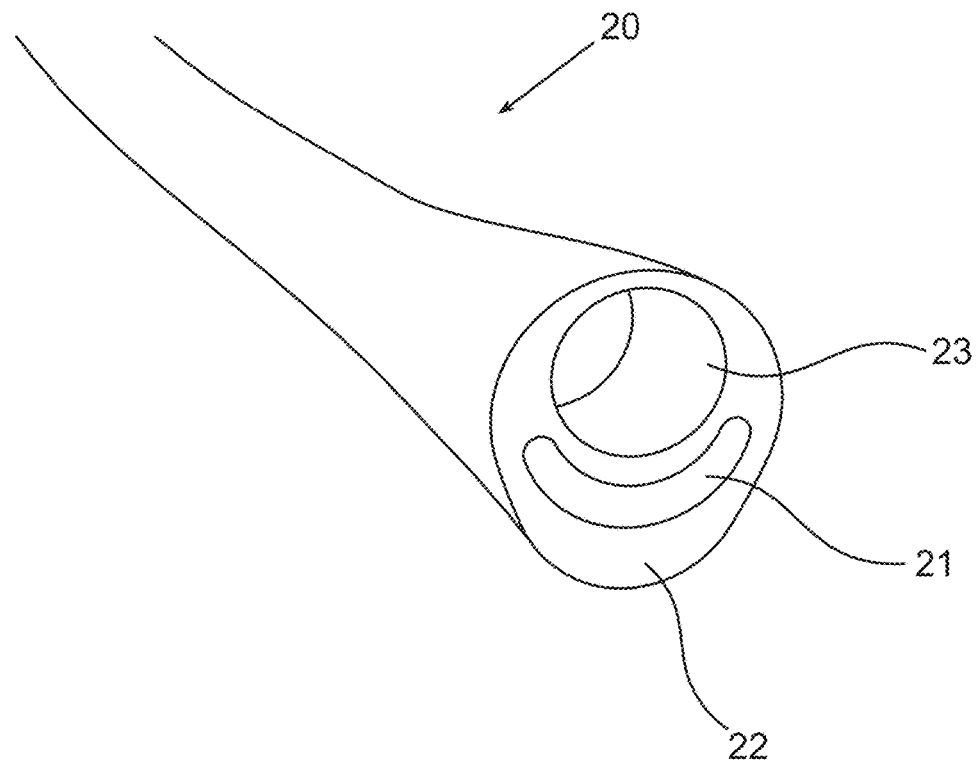
FIG. 2 schematically illustrates a perspective view of a head section of a hydro-dissection camera tool, according to another embodiment of the invention.

FIG. 2 shows a perspective view of head section of a hydro-dissection camera tool 20, according to another embodiment of the invention. The head section of hydro-dissection camera tool 20 comprises a water ejected port 21, a soft and flexible scrubbing element 22, and a camera 23 located at the distal end of tool 20. In this embodiment, tool 20 also has an elongated body thus it enables tool 20 to be used as a handpiece. According to some embodiments of the invention, the soft and flexible scrubbing element (e.g., as indicated by numeral 12 in FIGS. 1A-1C and as indicated by numeral 22 in FIG. 2) is optional, thus the hydro-dissection camera tool may not include such element.

In one embodiment of the invention, the flowrate of fluid through the water ejected port of the tool (e.g., as shown with respect to port 21 in FIG. 2) can be controlled by the width and angle of said tool. Furthermore, the water-flow can be pulsed or continuous, according to the surgeon's requirements. The flow may be directed by a pump that, for example, is either from a cataract removal unit or a vitrectomy unit. According to some embodiments of the invention, the tool may also have its own water source or pumping unit. The shape and cross section of the exit port of the fluid flow tips (e.g., water ejected port 21) can be of varied. During eye surgery if the effluent is too rapid, or its cross-section is too narrow, it may tear through the capsule of the eye. Furthermore, the pulsation rate and flow per pulsation has a dynamic effect in relation to the effluent width and height as well as the velocity of the effluent. If the pulsation rate is fast, the shock wave of effluent can tear through the capsule. According to an embodiment of the invention, these limits will be set into the device software flow software to limit the potential for capsular harm.

According to an embodiment of the invention, a soft scraping tool (such as elements 12 and 22 of FIGS. 1A-1C and 2, respectively) of any soft flexible material (e.g. silicone) that is curved at the base and side can be incorporated in to the tool to loosen cells that are strongly adhered to the capsule and which can be subsequently swept away with a reverse painting motion of the scraping tool. According to an embodiment of the invention, the tool may include a curved or straight section behind the tip of the head section to allow for gentle motion against the taught capsule for mechanically removing cells or loosening cells to then be swept clear by the tip.

In another aspect, the present invention relates to a medical ophthalmic device comprising a visualization probe with at least one camera (e.g., a video camera), wherein the sensor of the at least one camera is distally located at the tip of the tool to be inserted in to the eye for imaging from within the eye.

There is a considerable lack of standardization the terminology used in the literature related to digital video cameras in general and to those designed for use in endoscopic devices in particular. Herein, unless otherwise specifically mentioned, the following terminology will be used:

The terms "active area", "pixel/s area", and "array of pixels" are used interchangeably to refer to the light receiving surface of the array of photosensitive elements, e.g. photodiodes, that convert the incoming light into electrons.

The terms "sensor", "chip", "solid state image pick up device", and "image pickup device" are used interchangeably to refer to the active area; to the array of microlenses that concentrate the incoming light onto the photodiodes; to the array of filters, in the case of a color sensor; and to the silicon substrate on which the active area is created. In the case of sensors manufactures by a CMOS process, these terms also can include electronics adapted to deal with the output signals of the photodiodes that are implemented together with the array on the silicon.

The term "solid state imager" or in brief, "SSI", as used herein, indicates any suitable solid state image pick up device (for instance a CMOS or a CCD) that includes additional electronic circuits to generate additional functions of processing the signal on the same silicon or as an additional layer.

The term "camera head" refers to the SSI and associated optics required to focus the light on the active area encapsulated in a single package.

The terms "video camera", "camera" and "micro camera" are used interchangeably to refer to the camera head alone and also to the camera head and an additional electronic driver, if one is present.

The term "camera" refers exclusively to video cameras.

According to an embodiment of the invention, the miniaturization enables to obtain high quality images (for the purposes of example alone, in providing quality of at least 30 k pixels in relation to image sensors of the camera), while the body of the device is small enough to be inserted through an incision made around the cornea (e.g., during cataract surgery and MIGS). According to some embodiments of the invention, and for the purpose of example alone, the outer diameter of the device is about 1.8 mm or less, thereby enabling the performance of minimally invasive surgeries (i.e., enabling surgical techniques that limit the size of incisions needed and so lessen wound healing time, associated pain and risk of infection). The outer diameter of the device may vary in accordance with the dimensions of the elements/components that the device comprises. For example, the resolution of a camera may affect the camera's outer diameter, thus a high resolution camera may have a larger diameter than a camera with a lower resolution. Incision sizes less than 3 mm self-seal well and cause negligible refractive error and therefor depending on the task and need of the surgeon a larger camera can be easily accommodated with all the functionality of the tool, i.e., Illumination and hydro dissection and delineation. The present invention relates to a surgery device provided with an optic visioning means in a way that enables to miniaturize several components within one tool for microsurgery procedures. It also can be used in bimanual mode splitting the functions as required.

According to another embodiment of the invention, all features described herein can be incorporated into one tool where surgery is carried out through only one incision.

In the context of the present application the term "effective diameter" refers to the final diameter of the probe, regardless of its shape. Although in most cases the final shape of the probe would be circular, in spite of the fact that the SSI typically has a square or rectangular configuration, any other shape is possible and therefore the effective diameter could be equal to the longest cross-sectional dimension of the probe. Thus, for instance, for a probe having a square cross-section the effective diameter will be equal to the diagonal of the square, and the same arguments apply, mutatis mutandis, for a rectangular shape, an oval shape or a non-completed oval shape.

According to an embodiment of the invention the visualization probe comprises electronic circuitry (or driver), which is required to elaborate the signal generated by the SSI. In most of the cases the advantage of using a CMOS as an SSI, over the CCD, is the fact that it is easy and possible to implement several electronic circuits that embody several important features that are needed to generate the image or other features of digital processing—for example, correlated double sampling (CDS), A/D, gain, etc. These circuits are added in the design with the pure sensor that is built from pixels that are implemented with transistors in one package. The implementation of these pixels could be based on 2 transistors per pixel, 3, 4, 5, 6 and more or by using shared transistors or other designs, for example 2T2S or 4T4S, or higher degree shared transistors that implement the pixels. Obviously, these circuits extend the dimensions of the package and add more pads. In addition, if using signals with higher clock rate, it is advisable to use a driver that contains an amplifier or a regulator, a few capacitors for noise reduction, and some resistors to match signals. Such electronic circuitry (drivers) will add space in the package or the silicon and therefore in most of the cases it will be implemented externally to the packed CMOS or as an additional layer in the silicon construction.

If the CMOS has a diagonal smaller than 1.0 mm, the driver may contain parts of the image processing features, for example, correlation double sample (CDS) unit or other features needed to generate the image that were implemented in the packaged CMOS sensor itself and now are shifted externally to the driver or to the image processing unit. In such a case the CMOS sensor will contain only the implementation of minimal circuits that are needed to provide the signals and to pump out the raw signal from the CMOS. In addition, the driver will contain the minimum components required to match the clock signal needed to activate the CMOS and to pump the signal out to a video processing unit that now contains all needed circuits and components for processing the raw signal and transforming it to a video signal.

In this way, the CMOS sensor acts almost as a pure imager that transforms photons into electrons and its size is minimal. Since the driver also comprises the minimal number of components (one or two and sometimes the number could be zero), this ensures that the overall dimension of the new packaged CMOS video camera is minimal. The additional problem to overcome is the number of pads associated with the CMOS design and the cable (that contains all wires) which serves to provide the signals to activate the CMOS and to pump the signal out to the video processing unit. In the common practice there are several wires to provide these services.

Several technical solutions for reducing the imager's area to a minimum are described in U.S. Pat. No. 8,803,960. For example, since in a solid state imager with a diagonal smaller than 1.0 mm there is not sufficient space for so many pads, in order to overcome this problem it is necessary to set a minimal number of pads (ideally, one pad). By multiplexing several signals using the same pad, it is possible to use only 4 pads and sometimes 3 pads for the entire SSI. Another way of reducing the imager's area to a minimum is to change the methodology of the output video signal of the imager by using a current method instead of a voltage method. This also dictates that the external driver should include a matching stage circuit. The benefits from using such a method include better filtering of the noise associated with amplification and the ability to transmit the video signals over longer distances by using regulators controlled by the video processor to compensate for the video signal drop. Another example of a way in which the dimensions of a SSI can be reduced is to provide components on the silicon that have two functions, i.e. to grab the image and to transmit it. In addition to the above technical reducing solutions, compact configurations of CMOS chips, with and without PCBs, are disclosed in detail in WO2005/002210 and WO 2005/115221. The manufacturing of these assemblies are therefore not discussed herein in detail, for the sake of brevity.

Reference will now be made to several embodiments of the present invention, examples of which are illustrated in the accompanying figures. Herein several embodiments of the present invention are described for purposes of illustration only. One skilled in the art will readily recognize from the following description that alternative embodiments of the structures illustrated herein may be employed without departing from the principles of the invention described herein.

Figure 3A:
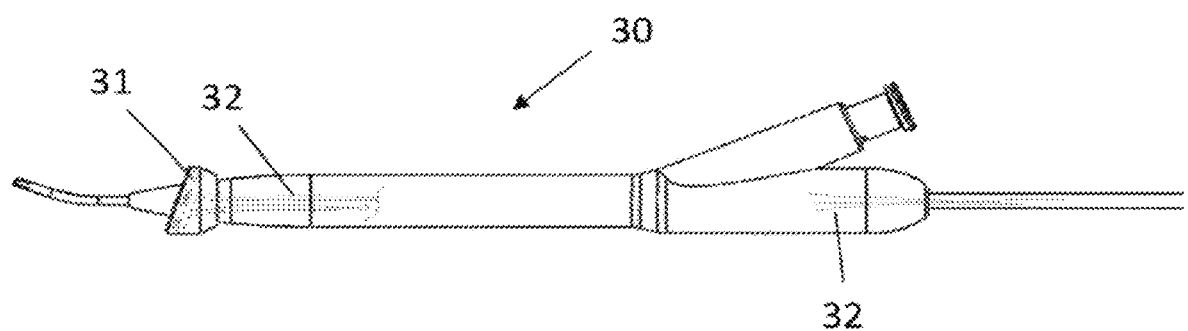
FIG. 3A schematically illustrates a side view of a medical ophthalmic device with an illumination source (e.g., like a plurality of LEDs, xenon arc lamp, etc.) located at the distal end of the device, according to an embodiment of the invention.
Figure 3B:
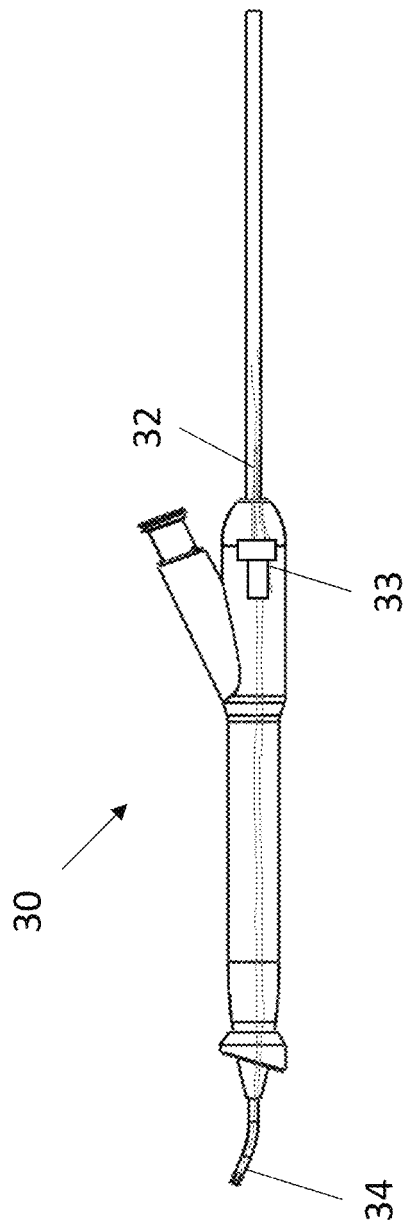
FIG. 3B schematically illustrates a side view of a medical ophthalmic device with illumination source showing the position of optic fibers located on the distal handpiece, according to an embodiment of the invention.
Figure 3C:
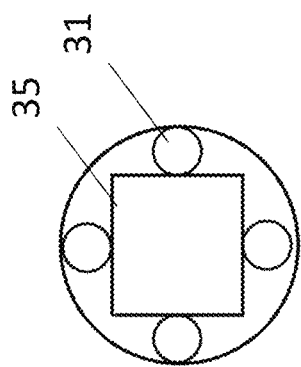
FIG. 3C schematically illustrates a cross-section view of the tip portion of the medical ophthalmic device of FIG. 3A, according to an embodiment of the invention.
Figure 7:
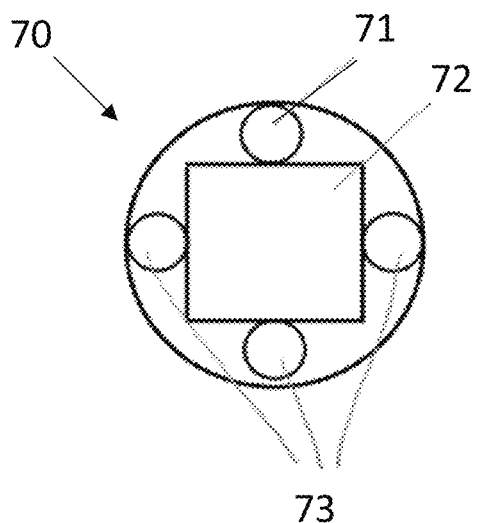
FIG. 7 schematically illustrates a cross section of the medical ophthalmic device provided with laser, camera and illumination, according to an embodiment of the invention.
Figure 8:
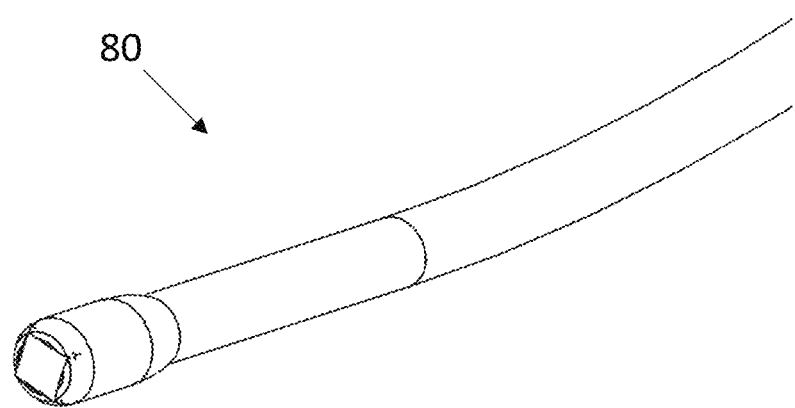
FIG. 8 schematically illustrates an olive type tip of a medical ophthalmic device, according to an embodiment of the invention.

According to an embodiment of the invention, the visualization probe comprises a camera that is incorporated into the medical ophthalmic device. An optical fibre attachment to these tools may broaden the scope of the utility, efficacy and functionality of the tool. In some embodiments, fibre optic or LED can be used to deliver light of varying colour and intensity to visualize the lens cells for removal, e.g., as shown with respect to FIGS. 3A and 3B. FIG. 3A schematically illustrates a medical ophthalmic device 30 with an illumination source 31 (e.g., like a plurality of LEDs, xenon arc lamp etc.) located adjacent to the distal end of device 30, according to an embodiment of the invention. For example, in case the illumination source 31 are one or more LEDs, and numeral 32 indicates the wiring from a power source or an illumination control module connected at the proximal end of device 30. FIG. 3B schematically illustrates the medical ophthalmic device 30 with illumination source that comprises LEDs and fiber-optics, according to an embodiment of the invention. In this embodiment of FIG. 3B, device 30 comprises an element 33 for coupling between LEDs and optic fibers 34. FIG. 3C schematically illustrates a cross-section view of the tip portion of the medical ophthalmic device of FIG. 3A that shows an arrangement of 4 LEDs 31 that surround a sensor 35 of a camera, according to an embodiment of the invention. FIG. 7 schematically illustrates a cross section view of a tip 70 of a medical ophthalmic device provided with a laser fiber 71, a camera 72 and an illumination source 73, according to an embodiment of the invention. FIG. 8 schematically illustrates an olive type tip 80 of a medical ophthalmic device, according to an embodiment of the invention.

In another embodiment of the invention, a light source can be placed: i) distally on the tool i.e., direct illumination, or ii) within the body of the tip including light-guides to the distal end, or iii) on the outer body of the tool with optical fibres guiding the light on to the target area, or iv) via an external light from a microscope, xenon lamp, xenon lamp/LED or other illumination source and optic bundle placed outside the eye, or v) using additional illumination, such as an endo-illuminator inserted into the eye in parallel to camera. Cells illuminated under different light wavelength will be stained differently and thus illumination is crucial for identification purposes. For example, the cells may be stained with blue or other stain at the conclusion of cortical clean up. The hydro-dissection tool equipped with a blue light source could then be used to illuminate adherent cells and to remove them by hydro-dissection, scraping or suction using a separate tool. According to embodiments of the invention, other staining means may also be used. For example, the tool may allow for mixing with staining material such as trypan blue 0.1%, gentian violet 0.001%, indocyanine green 0.5% (ICG). For example, the staining material can be mixed and jet together with the saline. The effluent may allow for mixing of the staining compounds. Compounds designed to reduce capsular collagen opacity may be applied after all cell layers are removed. By eliminating the current confounding issue of adherent cells, the natural history of the collagen and how if may be induced to remain clear will be better understood.

In another embodiment of the invention, a laser is incorporated into the tool to perform a variety of optical procedures e.g. measuring distance, laser cutting, photo-therapy, laser eye surgery, photo-ablation, etc. Furthermore, the wavelength of the laser light can be varied for the specific requirements of the task. Low energy laser light may be helpful in identifying adherent cells without the need for staining compounds.

In another embodiment of the invention, an ultrasound tool is incorporated to the device for emulsifying lens.

Since the light source can be external, the tool is compatible with any externally connected light source. For example, see FIG. 3A and FIG. 3B. The ability to see the cells at the angle of the tip of the instrument allows the surgeon to complete the task of cell removal in areas of the eye that are not visible currently from the microscope above. The cross illumination of LEDs and the chromatic fiberoptic combined with video observation are key to the performance of the tasks that the tool is capable of. The angle and placement of the video camera is not limited. Typically, the video camera may be 1.0 mm size (or even less than 1.0 mm) and incorporate the vacuum part of the bimodal system or the ejection component or both. This unit may have a slit opening for vacuum of 0.2 mm or greater and may be 1.8 mm wide. FIGS. 3A-8 show a variety of options available for the positioning of the camera and light source i.e., the light source can be external and guided by light guides and/or optical fibers, or integrated distally on the tip itself (i.e., internally). For example, FIGS. 4A and 4B show an arrangement in which an illumination source 41 and a camera 42 are located at a tip 40 of a medical ophthalmic device, according to an embodiment of the invention. In this arraignment, illumination source 41 located on top of camera 42. FIG. 5 schematically illustrates a side view of a tip 50 of a medical ophthalmic device with camera 52 and LED 51 on the same PCB 53 in one embodiment, according to an embodiment of the invention. FIG. 6 schematically illustrates a side view of a tip 60 of a medical ophthalmic device with a camera 61 and LED 62 behind it, according to an embodiment of the invention.

The light source itself can include, but is not limited to: a microscope light, incandescent bulb, operating room light, light emitting diode (LED), fluorescent bulbs, xenon arc lamp, and the like; which can be used individually or in combination. According to an embodiment of the invention, the light source is in form of a light probe that is adapted to be inserted in parallel to the device. Having light sources of different types available is important because surgical procedures often require procedure-specific lighting. Furthermore, light illumination can be facilitated by light guides and optic fibres (see FIG. 3A and FIG. 3B). In addition, the colour of the light source is not limited to white light alone, but can include any colour and or wavelength that assists the user in carrying out the procedure. According to an embodiment of the invention, a removable/replaceable distal tip may include one or more LEDs with different wavelength. For example, the colour can be managed by software when RGB LED used.

In one embodiment of the invention, the flowrate of fluid through the tool can be controlled by the width and angle of said tool. Furthermore, the water-flow can be pulsed or continuous, according to the surgeon's requirements. The flow may be directed by a pump that is either from the cataract removal unit or the vitrectomy unit. It may also have its own source. The shape and cross section of the exit port of the fluid flow tips can be of varied. During eye surgery if the effluent is too rapid, or its cross-section is too narrow, it may tear through the capsule. Furthermore, the pulsation rate and flow per pulsation has a dynamic effect in relation to the effluent width and height as well as the velocity of the effluent. If the pulsation rate is fast the shock wave of effluent can tear through the capsule. The limits of these energies will be set into the software of the pump to prevent the surgeon from exceeding these limits. See FIGS. 11-13 for examples of embodiments of the invention wherein fluid passes between the optic fibers and/or the camera which is arranged at the distal tip and the openings define the flow direction and pressure.

In another embodiment of the invention, a soft scraping tool of any soft flexible material (e.g. silicone) that is curved at the base and side can be incorporated in to the device to loosen cells that are strongly adhered to the capsule and which can be subsequently swept away with a reverse painting motion of the scraping tool. The device may include a curved or straight section behind the tip to allow for gentle motion against the taught capsule for mechanically removing cells or loosening cells to then be swept clear by the tip.

In another embodiment of the invention, the tip may be angled to allow for sub capsular angulation as needed and may be sleeved to allow for inflow to or from an outer sleeve. The fluiditics passing through the tip flows at rate that is proportional to resistance/flow. If the flow remains constant, then the resistance increases the pressure which in turn causes the fluid to eject at a faster rate. In general, an object of this invention is to create a flat or slightly curved fluid plane that will encounter resistance as it flows against the lenticular capsule. The resistance will be adherent cells and viscoelastic that is remaining in the aqueous fluid of the anterior and posterior chambers. Therefore, the shape of the tip is essential to the concept of this tool.

Figure 9:
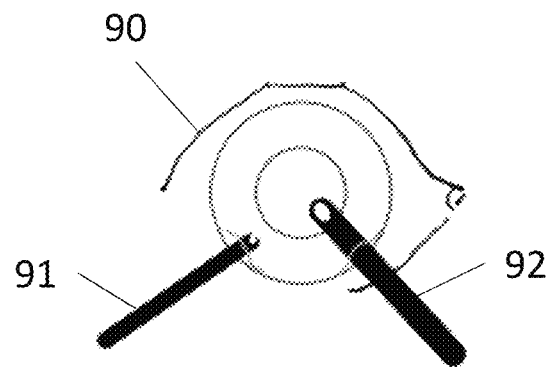
FIG. 9 schematically illustrates bi-manual mode.

In another embodiment of the invention, the ejection portion of the device may be separated from the suction or return portion in a bi-manual version. In this way the ejection portion size may be reduced to allow for it to be placed through a smaller incision as in the side port or an additional incision. See FIG. 9 for a depiction of this embodiment, in which bi-manual mode is used with a camera and irrigation tool 91 are inserted into an eye 90 via a secondary incision, while an aspiration tool 92 is being inserted in eye 90 via a primary incision.

In another embodiment of the invention, the suction portion of the unit may incorporate the light source, the video camera or the injection unit for placing staining compounds onto the capsule. The staining material could be used to visualize lens cells as well as residual viscoelastic. The use of chromatic light on the device will enhance visibility of residual cells. As this tool places visibility behind the iris it may be equipped with an attachment for placing grasping or cutting tools for performing procedures out of sight from the microscope above.

Figure 10:
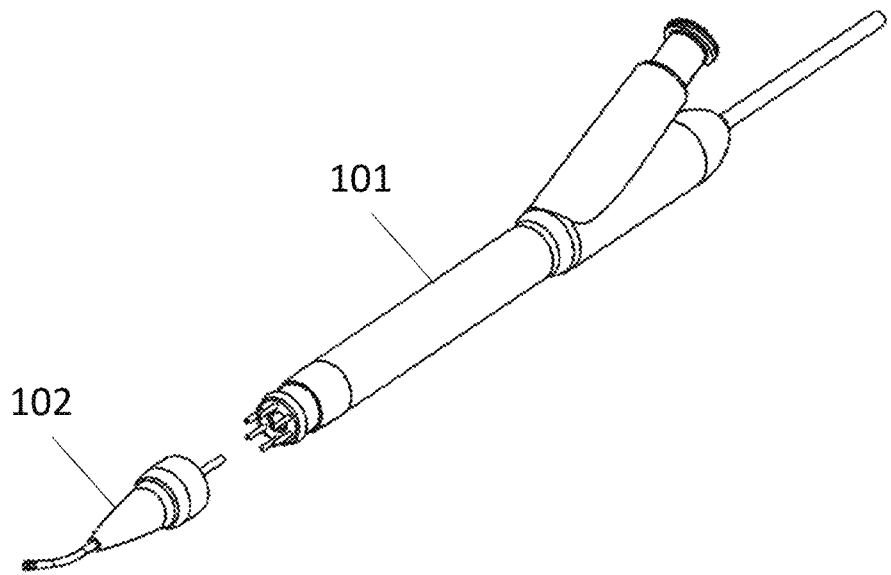
FIG. 10 schematically illustrates a disposable tip with reusable handpiece, according to an embodiment of the invention.

In another embodiment the camera is integrated into the tool which uses irrigation and aspiration. The camera and illumination may be integrated into the irrigation tool only (bimanual method for cataract surgery). For the purposes of example alone, the irrigation channel may be at least 0.3 mm with any cross-section shape (e.g. a few small tubes or in the free space between the components in the outer tube). For example, the outer diameter can be about 1.5 mm. The tool could also be inserted through the primary and/or secondary incision. According to the convenience of the surgical practice, the tips can be either permanent (reusable) or detachable (disposable). See FIG. 10 for a depiction of a disposable tip 102 with a reusable handpiece 101.

Figure 11:
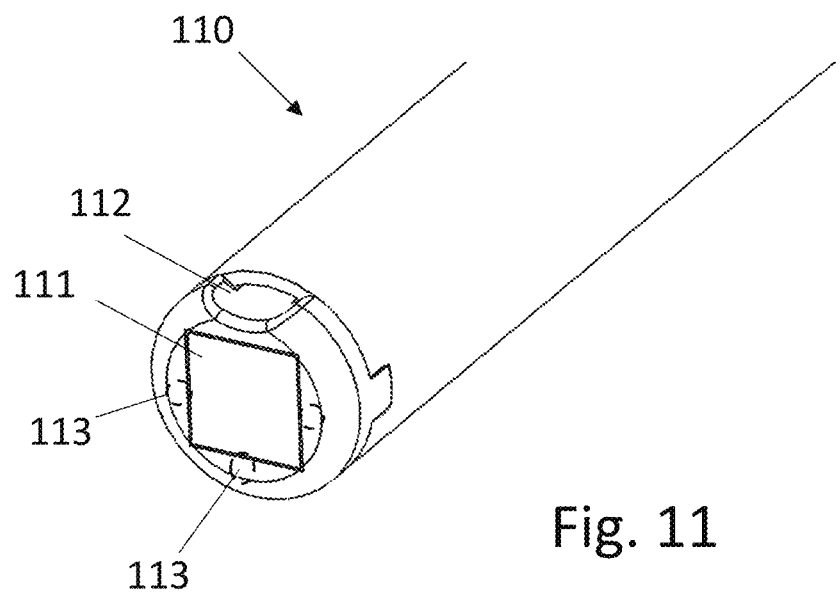
FIG. 11 schematically illustrates the distal tip of a medical ophthalmic device provided with an opening for irrigation or vacuum, according to an embodiment of the invention.
Figure 12:
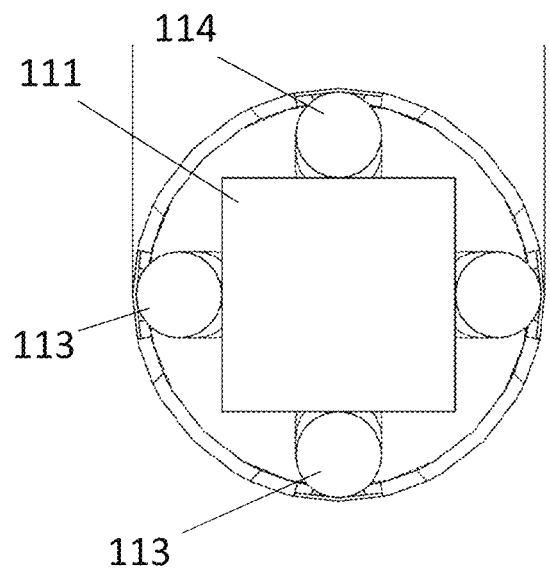
FIG. 12 schematically illustrates a cross-section of an irrigation tube of the medical ophthalmic device of FIG. 11, according to an embodiment of the invention.
Figure 13:
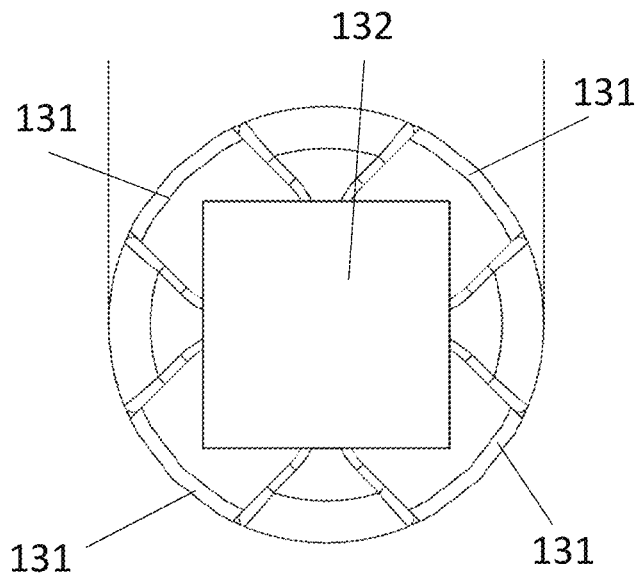
FIG. 13 schematically illustrates a cross section of the distal tip showing openings for irrigation or vacuum, according to an embodiment of the invention.

FIG. 11 schematically illustrates a medical ophthalmic device 110 provided with an opening 112 for irrigation or vacuum, according to an embodiment of the invention. Medical ophthalmic device 110 comprises a camera 111, an opening 112 for irrigation or vacuum and illumination sources 113. FIG. 12 schematically illustrates a cross-section of the tip of medical ophthalmic device 110 that shows an irrigation tube 114, according to an embodiment of the invention. In this embodiment, the water flow through irrigation tube 114 and ejected via opening 112. FIG. 13 schematically illustrates a cross-section of a distal tip of a medical ophthalmic device showing openings 131 for irrigation or vacuum that are arranged around a camera 132 located at the center of the tip, according to another embodiment of the invention.

Figure 14:
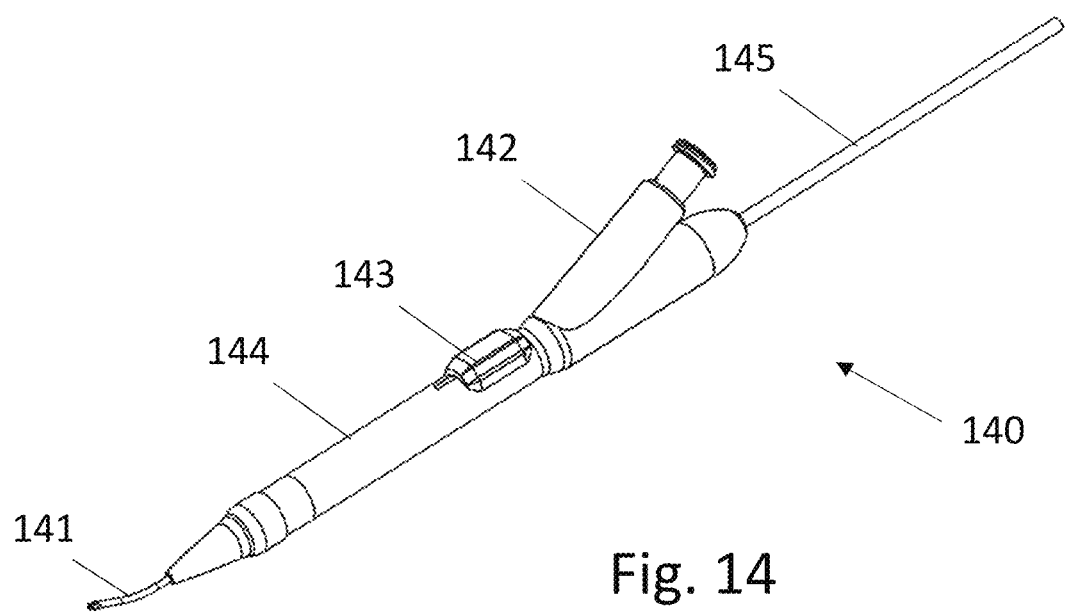
FIG. 14 schematically illustrates a medical ophthalmic device provided with irrigation and a camera sensor located at the tip of the device, according to another embodiment of the invention.

FIG. 14 schematically illustrates a medical ophthalmic device 140, according to another embodiment of the invention. Device 140 comprises an irrigation port 142, a tip 141 on which a camera sensor (not shown) is located. The flow rate can be controlled via a flow rate controller 143 located on the body 144 of device's handpiece. In this embodiment, device 140 is controlled and powered via an operation unit (not shown) that is electrically connected to device 140 via cables 145.

Figure 15A:
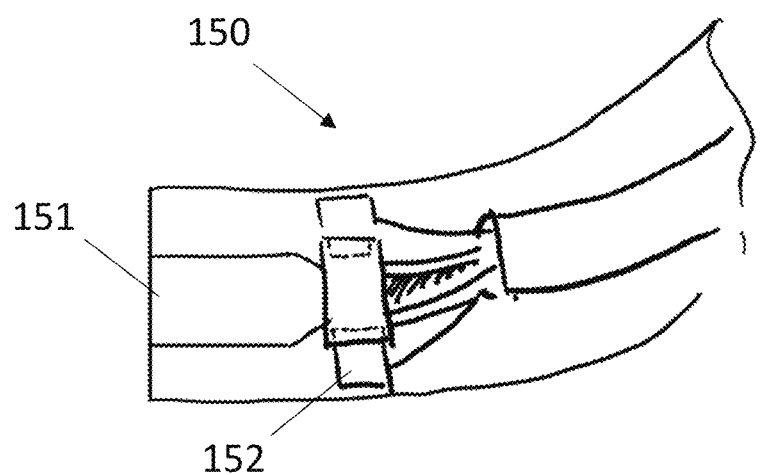
FIG. 15A-15B schematically illustrate a medical ophthalmic device with plurality of LEDs and a camera located at proximal end of handpiece, according to an embodiment of the invention.
Figure 15B:
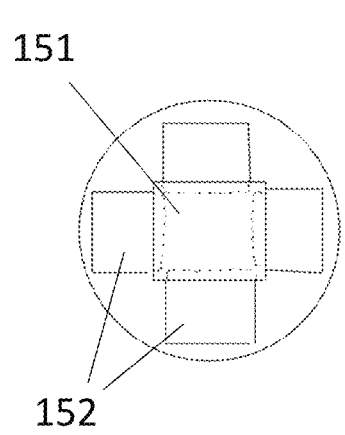
Figure 16:
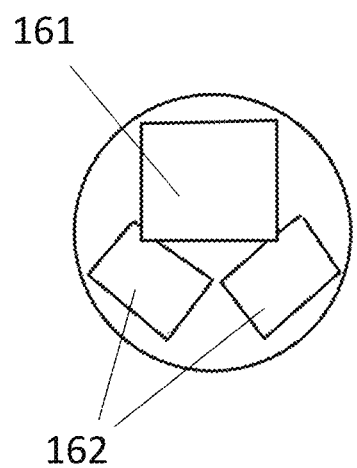
FIG. 16 schematically illustrates a cross-section view of another arrangement of a camera and a plurality of LEDs located at proximal end of a handpiece of a medical ophthalmic device, according to an embodiment of the invention.

FIGS. 15A-15B schematically illustrate a medical ophthalmic device 150 with plurality of LEDs 152 and a camera 151 located at proximal end of handpiece, according to an embodiment of the invention. FIG. 16 schematically illustrates a cross-section view of another arrangement of a camera 161 and a plurality of LEDs 162 located at proximal end of handpiece.

In another embodiment of the invention, the tip may be angled to express the sheet of fluid in a downward or upward direction. It can be angled against the surface of the membrane putting minimal tension on the capsule while "peeling" off the debris and lenticular cells that remain adherent. Therefore, the tip gap and width are very important to the function and safety of the device. The width and gap of the tip will have several variations and the user will be able to select the tip that best suits their experience and goal. For the purposes of example alone, the tip can be 0.5 mm to 2.5 mm in width. For the purposes of example alone, the gap can vary from about 0.05 mm to 1 mm and may include a curved or straight shape. The tip may also have a roughened under-surface to allow for loosening of the cells from the surface behind the jet of fluid. In this way the capsule may be flattened in front of the roughened area to reduce the risk of the capsule rolling or folding and then snagging and tearing. The roughened area may also be widened to allow for a widened surface area to be cleared or loosened ahead of the hydro-dissection cannulated tip that is following. In this way the risk of stroking the delicate capsule is decreased.

In another embodiment of the present invention the material of the tip may be metal with a combination of soft polymer elements to allow gentle scarping.

Furthermore, the tip may have adjustable stiffness enabled by piezo elements, removable metal wire inside, using two tubes, outer rigid tubes and a pre-shaped semi-rigid or flexible inner tube. By this method, the tip may be turned to provide variable views from the camera and to direct flow.

The present invention enables procedures wherein lens fragments are removed under direct vision. This can be done with the following combination of components, but is not limited to this list alone: a camera with irrigation, a camera with aspiration, a camera with irrigation and aspiration, a camera and phacoemulsification ultrasound probe, a camera and feature allowing length accurate rotating and positions.

The present invention enables glaucoma surgery. A camera can remove the need for using a gonioscope since it can provide visualization of ciliary sulcus and sub iris space. In this use the camera can be attached to a therapeutic device and also to be the diagnostic observational device inserted through the second incision. The camera can also be placed in parallel with a therapeutic device such as a stent delivery tool, shunt delivery tool or the shunt itself. According to some embodiments of the invention, the camera can be integrated to implant delivery tool.

The present invention enables vitrectomy procedures wherein a camera inserted into the eye can serve as a visualization tool when an anterior segment of the eye is opaque (e.g. an opaque cornea). In this embodiment, the camera is small enough to pass through the trocar used in surgery and can assist in positioning sutures, removal of intraocular foreign bodies. For anterior procedures curved tips can be used whereas to vitreoretinal procedures straight tips can be used.

A curved band which may be made of flexible material like silicone can be placed behind the ejection zone. This can be used to stroke the tissue that is being flattened out in front of the effluent. The curved zone behind the tip may be a hard material based on the surgeon's preference for the required task.

The curved tip may mimic the posterior curve of the capsule. The ideal angulation of the tip for hydro-dissection may be effectively parallel or (for the purposes of example alone) may also be angled at 5 to 25 degree or more. This may be accomplished by angling the external instrument or may be built into the tip with the scarping element whether (e.g. silicone) or rough (e.g. diamond) or a rough synthetic or metal surface.

Typically, the water inflow is matched by outflow through the sides of the device or by a "bi-manual" technique. In bi-manual mode two tools are used to irrigate and aspirate. In bi-manual mode the two separate tools are inserted in to two separate incisions and operate simultaneously. According to an embodiment of the invention, the tool may comprise both irrigation and aspiration via adjacent channels on the same tool, i.e., without the need for two separate tools. In this embodiment the operation of the irrigation aspiration device is reversed with outflow from the tip and return flow along the side of the instrument. The tip may also be used as a tool to work against a distended capsule which is less at risk of snagging and tearing. The viscoelastic can be fully ejected from behind and in front of the IOL as well as into the iris sulcus and the dome of the cornea.

In another embodiment of the invention, as well as the bi-manual approach, water inflow and outflow can also be controlled via the same tool. In this approach, irrigation and aspiration can be carried out by a) two parallel tubes, or b) a coaxial method. The two parallel tube method has the advantage of being able to place the tube inlets and outlets anywhere on the distal end of the probe e.g., next to each other, or far apart; whereas the coaxial method aids in miniaturization, by saving volumetric space along the probe itself but also at the distal end of the probe. The coaxial method involves concentric tubes wherein the central tube irrigates and outer tube aspirates, or vice versa. Both methods have the advantage of being miniaturized and integrated into a single tool, without the need for a second tool through the secondary incision.

The tip may be used for sub-incision clearance as well by directing the flow from the side port or secondary incision. The more completely the eye is cleared of cells the fewer the repercussions expected at the recovery stage.

Lens particles, cortical and viscoelastic material are often concealed underneath the iris. Reaching these with a suctioning tool can lead to damage to the capsule resulting in zonular dehiscence or capsular rupture. The superior advantage of power washing versus suction is safety and effectivity. Staining and illumination allow visualization and confirmation of removal. Any retained lens material even thin layers of cells but in particular nuclear material will lead to chronic or acute inflammation which can cause slow recovery or macular swelling or cystoid macular edema. Therefor fully clearing these cells completing the cataract removal predicts for better post-operative outcomes.

In one embodiment of the invention, the device can be equipped with an attachment beyond the camera like a forceps or scissors and would allow the surgeon the capability of performing tasks under direct visualization. This could include suturing in a capsular tension ring or a secondary IOL and for releasing an IOL from its capsular attachment. The water ejection system could maintain pressure and eliminate the need for viscoelastic in some of these procedures. The intraocular lens is centered by it arms or haptics protruding out to the capsular support area of zonular capsular connection. How the IOL is seated in this zone is currently not visualized. If it were the haptics could be adjusted to optimally place them in the proper and strongest position under direct observation. Furthermore, when an IOL must be removed to be able to separate the tissue planes of the capsule folding over the haptic would facilitate a much safer and controlled procedure. In some case the zonulas are weak and will tear loose from their ciliary body attachment. In these cases, a ring can be placed into the capsular bag to equalize the stress around the compromised bag. To directly visualize the ring and area needing support would optimize the use these cases. At time a suture must be placed or the haptic "lassoed" to attach it to the sclera. Under direct observation this procedure would again be optimised. In a case where both hands were needed the device could be stabilized into position to view the area of interest while the surgeon used both hands to suture or tie a knot.

In one embodiment of the invention the fluid projection from the device's tip can be shaped to allow hydro dissection of lens cells safely from the lenticular capsule with less volume of fluid required. This can be controlled via a foot pedal or from the handpiece itself. An example of such an embodiment of the tool is shown in FIG. 15 where various buttons, levers and valves are shown integrated into the tool, to control the flow rate and other parameters that are described herein. The flow rate may be adjusted based on the requirements of the task and at the discretion of the surgeon. The flow may be pulsed or continuous according to the requirements of the task and at the discretion of the surgeon. Accordingly, the frequency and intensity of the pulse can be set by the surgeon as well. For the purpose of example alone, the frequency of pulsation may be a low rate of a pulse per second or a fast rate of 10 or greater pulses per second. Furthermore, the fluid flow rate and pulse rate can vary independently. By varying the flow- and pulse-rate the device will adapt to the experience and the tissue differences encountered. The pulsation rate may be controlled by different methods. The pump can stutter in its pump movement, a valve can occlude either flow line course or in the handpiece itself. Such methods are well understood by one knowledgeable of the arts of fluid flow and the above examples are not limiting.

Figure 17:
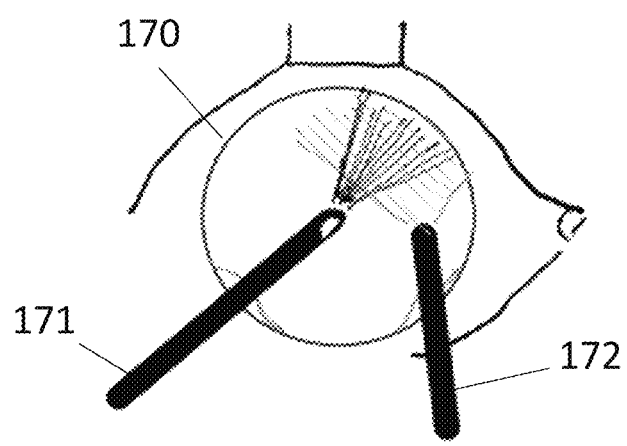
FIG. 17 schematically illustrates combined camera and irrigation probe working together in parallel with a light probe within a human eye, according to an embodiment of the invention.

FIG. 17 shows another embodiment of the invention that demonstrates the use of two devices simultaneously. FIG. 17 schematically illustrates combined camera and irrigation probe 171 working together in parallel with a light probe 172 within a human eye 170. Typically one to two incisions (normally called the 'primary' and 'secondary' incisions) of less than 3 mm are made in the eye during surgery. The device described herein is fitted such that it seals the incision and enables pressure to be retained in the eye during surgery. The two incisions enable the use of two separate devices to be used simultaneously during surgery. For the purposes of example alone, the two devices can be a combination of a number of different features. The first tool can incorporate a camera and irrigation tool inserted in one incision and the second tool can incorporate an illumination probe. An expert in eye surgery will see the utility in such an approach and be able to devise other combinations of features for both tools. For example light illumination (of any wavelength), lasers, irrigation, scraping elements, cameras and other, can be integrated in to either tool in any combination. The unique miniaturized features of the present invention enable the combination of such features to allow the necessary flexibility for an expert in eye surgery to operate optimally.

Figure 18:
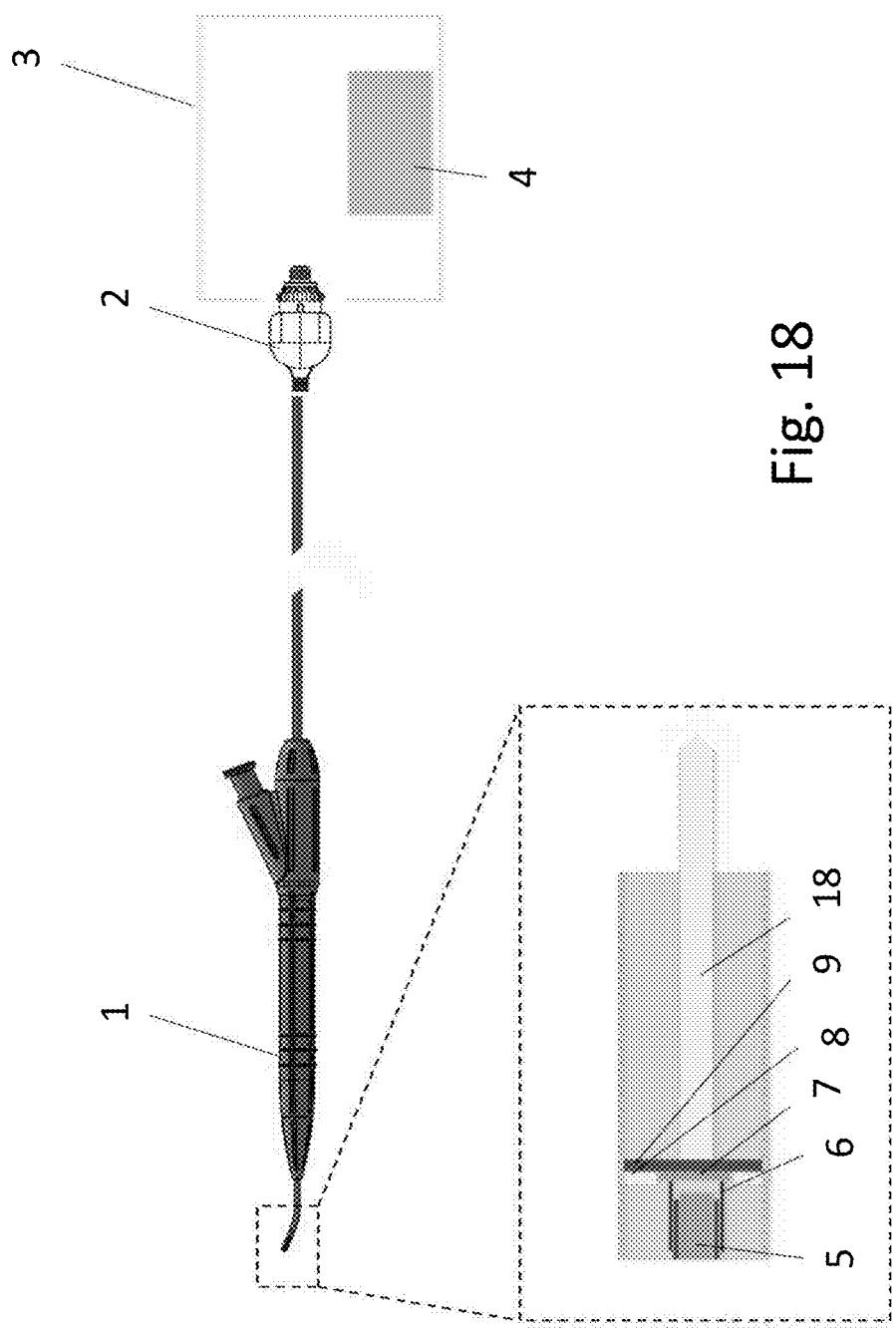
FIG. 18 schematically illustrates a medical ophthalmic device with various components, according to an embodiment of the invention.

FIG. 18 shows an embodiment of the invention that demonstrates the miniaturization capability of the medical ophthalmic device as well as the different components/units. A handpiece 1 is connected via suitable connector 2 to an endoscopy unit 3 and video controller 4. The endoscopy unit 3 includes several features, but is not limited to the following: white light balance and light intensity controllers, capturing photo-stills and/or live video recording. Furthermore, irrigation regulation and control can be provided through this unit or may be included in a separate unit. Said endoscopy unit is compatible with all electrical connections such as HDMI, DVI, composite, S-Video and USB, but is not limited by this list alone. In this embodiment, the probe consists of various components integrated together at the distal end of the probe unit. In this embodiment, an optic barrel 5 is built of two or more lenses and can contain any number of filters and or/coatings to control any aspect of illumination (e.g. intensity, frequency/wavelength, temporal light intermittence, waveform, etc.) according to a particular need. A sensor housing 6 and the optical barrel 5 can be integrated together or separated, according to the optical requirements of a particular procedure. A sensor 7 can be wafer-based i.e., camera, sensor and optical barrel are integrated/assembled as one piece, or using more conventional methods wherein the optical components are separated from the sensor itself and the focusing lens can be adjusted by changing the distance between their surfaces. One or more LEDs 8 are integrated in to the distal end of the probe device on a Printed Circuit Board (PCB) 9. The light source can also be provided by optical fibres from an external light source unit to the distal end of the probe. The LEDs can be placed where its surface and the distal surface of the optical barrel are flush to further save volumetric space in aiding miniaturization. The LEDs 8 can also be placed on the same PCB as the sensor 6. Furthermore, the camera can also operate without any illumination; such an option may be important in order to further miniaturize the device for high resolution precision surgery. In the option without the illumination features described herein, the probe can operate with a camera at a much smaller scale due to the space saved and subsequent miniaturization. Alternately a larger chip could be used to give higher resolution from the same incision requirements. A cable 18 connects all features throughout the device, from the distal end of the probe, where many of the functional components are located, to the handpiece and external measuring units. A flexible design PCB can be implemented to replace the cable. The PCB can be angled at 90 degrees and, in another option, two PCBs can be used. Said cable 18 connects to the video controller 4 in the endoscopy unit 3. Furthermore, a miniature videocontroller can be placed on the handpiece itself and integrated into the device.

According to an embodiment of the invention, the tip of the probes may be bendable to allow them to be bent in a U shape to look under the incision and by rotation in the zones left or right of the area of interest. In this embodiment the probe support would be made of conformable material like metal or polyamides.

The probe may have lateral support cords to allow for pulling the cord in a lateral direction to cause the tip of the probe to rotate in one or two direction. As the probe is round rotation and the ability to bend the tip would allow for pointing the probe in any direction needed. Because of the relatively small space that is the internal eye minimal bends and rotation can direct the tip to point in any direction needed.

The optical design of a complete objective takes into account several parameters, for example: the Field Of View (FOV), the Depth of Field (DOF), the pixel dimension, the effective area of the sensor, and the orientation of its optical axis in comparison to the mechanical axis of the entire solid state sensor camera head. For the sake of simplicity of this description, it is assumed that these two axes coincide; if they do not coincide, a shift in mechanical part and/or assembly must be considered, or in case of aspherical lenses the mold for the lenses can take this shift into consideration. Other parameters also affect the design, for example the level of distortion and F number. If the distortion is too high, then a 'fisheye' effect appears and if the F number is too high, more illumination is needed to receive a bright image. Software driven magnification could allow for enlargement of an area of interest. The use of OCT on the in place of the video probe could be used conjunction with the device to give views through the tissue plane when deemed necessary.

In one embodiment of the invention the probe is attachable onto a medical ophthalmic device. According to this embodiment, therefore, it is possible to provide medical ophthalmic devices which are reusable, i.e., which can be sterilized and used in subsequent procedures, while the visualization probe can be disposable. This is made possible by the low cost attainable by employing the methods described herein to manufacture embodiments of visualization probes according to the invention. Examples could be the phaco tip, a side port probe used for chopping the cataract or manipulating an implant, attaching to a MIGS inserter.

In another aspect, the invention is directed to a medical ophthalmic device comprising a socket or channel suitable to house a visualization probe having an imager, e.g., with an outer diameter of about 1.8 millimeters or less. In such a device the socket may comprise signal transfer connectors adapted to receive signals generated by the probe and to transmit them to display equipment.

The term "medical ophthalmic device", as used hereinabove, refers not only to devices which are used to actively perform surgical procedures on the human or animal eye, but also to devices which are used for diagnostic purposes only and to devices used for delivery of therapy and/or drugs. Any device which is introduced into an eye of an animal or human body comes under the definition of medical device throughout this specification. Such medical ophthalmic devices may be selected, for instance, from among endoscopes; scissors; scalpels; laparoscopes; flexible, semi-flexible, semi-rigid, or rigid single or multi-lumen tubes (or pipes), used for therapeutic procedures or to protect the eye when inserting and extracting other devices through these tubes (or pipes); springs; rods; devices that are used for approximating, cutting, and sealing tissues; devices for burning, coagulating, or in other ways destroying objects; devices for feeding, guiding, draining, or delivering objects or substances; guidewires, forceps, monitoring and/or diagnosis devices; wireless in vivo devices, etc.

The invention further encompasses the combination of a medical ophthalmic device and of a visualization probe as described above. For example, the solid state imager can be located at the distal end of a visualization probe that is attached to a surface of the medical ophthalmic device.

The objectives of the invention, i.e. to produce very small size visualization probes and medical ophthalmic device that contain them, have been attained by utilizing the techniques described herein above.

As will be apparent to the skilled person all the above description and examples have been provided for the purpose of illustration and are not intended to limit the invention in any way. The probes of the invention can be employed to create many different surgical tools, and many such different tools can be created, which comprise sockets adapted to receive probes, according to the invention, at various locations as appropriate and convenient according to the different tools and procedures employing them. Accordingly, the invention opens the door for a new generation of medical devices in particular medical ophthalmic devices, without limitation to their shape, location of the probes and their intended use. It is also possible to "install" the probe without housing or to install a probe that already contains a housing in the tool.

The invention claimed is:

1. A medical ophthalmic endoscopic device comprising at least one camera, wherein a sensor of the at least one camera is located at a distal end of said endoscopic device, wherein said camera and one or more components/tools are integrated in the endoscopic device,
wherein the outer diameter of said endoscopic device is about 1.5 mm or less,
  wherein the camera is located at a center of the distal end and the one or more components/tools are arranged around the camera, and
  wherein the camera has a rectangular shape and the distal end has a circular shape,
  the endoscopic device further comprising a handpiece and a flattened distal tip configured to receive fluid flow from a pumping unit and generate a jet of fluid suitable for hydro-dissecting cells in an eye of a subject, wherein the fluid flow is controllable by a control unit configured to allow variations in the fluid flow to the flattened distal tip.

2. The device of claim 1, wherein the endoscopic device is configured to be inserted through an incision made around a cornea of an eye of a subject during a procedure of cataract surgery and/or Minimally Invasive Glaucoma Surgery (MIGS).

3. The device of claim 1, wherein the endoscopic device is configured to be inserted through a trocar.

4. The device of claim 1, wherein the one or more components comprise one or more illumination sources.

5. The device of claim 4, wherein the one or more illumination sources comprise one or more LEDs, the one or more LEDs are located around the sensor.

6. The device of claim 4, wherein the one or more illumination sources are located proximally in the device thus light reaches the distal end of the endoscopic device via one or more optic fibres and/or one or more light guides.

7. The device of claim 1, comprising a camera located at a distal end of the endoscopic device, one or more illumination sources located proximally in the device and one or more optic fibres and/or one or more light guides providing light from the illumination source to the distal end of the device.

8. The device of claim 7, wherein the one or more optic fibres and/or one or more light guides are arranged around the sensor at the distal end of the device.

9. The device of claim 1, wherein the one or more components/tools comprise an irrigation channel.

10. The device of claim 9, comprising a camera located at a distal end of the endoscopic device; one or more illumination sources located proximally in the device; one or more optic fibres and/or one or more light guides providing light from the illumination source to the distal end of the device; and one or more irrigation channels.

11. The device of claim 10, wherein the one or more optic fibres and/or one or more light guides and the one or more irrigation channels are arranged around the sensor at the distal end of the device.

12. The device of claim 1, wherein the one or more tools comprise a phaco-emulsifier tool and/or a tool for removing lens cells under direct vision.

13. The device of claim 12, wherein the tool for removing lens cells comprises an irrigation tool, an aspiration tool, or a combination thereof.

14. The device of claim 13, wherein the irrigation and aspiration tools are integrated together in concentric circles, one in an inner circle and one in an outer circle, or they are located adjacently.

15. The device of claim 1, wherein the handpiece comprises a valve configured to block or release the fluid flow, thereby facilitating control of a flow rate.

16. The device of claim 1, wherein the valve is further configured to facilitate continuous or pulsed fluid flow.

17. The device of claim 1, wherein the flattened distal tip is replaceable to control the fluid flow rate, pressure, velocity and/or trajectory.

18. The device of claim 1, wherein the flattened distal tip is straight, curved or bendable.

19. The device of claim 1, wherein the flattened distal tip is divided to facilitate separate fluid flow and suction.

20. The device of claim 1, wherein the flattened distal tip is rotatable.

21. The device of claim 1, wherein the size of an opening of the flattened distal tip is between about 0.5 mm-1 mm.

* * * * *